(12) United States Patent
Clune et al.

(10) Patent No.: US 7,406,215 B2
(45) Date of Patent: Jul. 29, 2008

(54) METHODS AND SYSTEMS FOR CORRECTING IMAGE MISALIGNMENT

(76) Inventors: Thomas Clune, 53 Central St./P.O. Box 827, Ashburnham, MA (US) 01430; Philippe Schmid, Grand-Rue 4, CH-1071, Chexbres (CH); Chunsheng Jiang, 28 Benton Cir., Reading, MA (US) 01867

(*) Notice: Subject to any disclaimer, the term of this patent is extended or adjusted under 35 U.S.C. 154(b) by 0 days.

(21) Appl. No.: 11/633,677

(22) Filed: Dec. 4, 2006

(65) Prior Publication Data
US 2007/0147705 A1    Jun. 28, 2007

Related U.S. Application Data

(60) Division of application No. 10/273,511, filed on Oct. 18, 2002, now Pat. No. 7,187,810, and a continuation-in-part of application No. 10/068,133, filed on Feb. 5, 2002, which is a continuation of application No. 09/738,614, filed on Dec. 15, 2000, now Pat. No. 6,902,935.

(60) Provisional application No. 60/414,767, filed on Sep. 30, 2002, provisional application No. 60/170,972, filed on Dec. 15, 1999.

(51) Int. Cl.
*G06K 9/32* (2006.01)
*G06K 9/00* (2006.01)

(52) U.S. Cl. .................................. 382/294; 382/128
(58) Field of Classification Search ......... 382/128–134, 382/294, 278, 289, 312; 600/310, 410, 443, 600/476; 324/309
See application file for complete search history.

(56) References Cited

U.S. PATENT DOCUMENTS

| | | | | |
|---|---|---|---|---|
| 5,003,979 | A | * | 4/1991 | Merickel et al. ............ 600/410 |
| 5,690,106 | A | * | 11/1997 | Bani-Hashemi et al. ...... 600/425 |
| 6,004,270 | A | * | 12/1999 | Urbano et al. .............. 600/443 |
| 6,292,683 | B1 | * | 9/2001 | Gupta et al. ................ 600/410 |
| 6,445,182 | B1 | * | 9/2002 | Dean et al. ................. 324/309 |
| 6,445,943 | B1 | * | 9/2002 | Ferre et al. ................. 600/424 |

* cited by examiner

*Primary Examiner*—Kanji Patel
(74) *Attorney, Agent, or Firm*—Fish & Richardson P.C.

(57) ABSTRACT

The invention provides methods of determining a correction for a misalignment between at least two images in a sequence of images due at least in part to sample movement. The methods are applied, for example, in the processing and analysis of a sequence of images of biological tissue in a diagnostic procedure. The invention also provides methods of validating the correction for a misalignment between at least two images in a sequence of images of a sample. The methods may be applied in deciding whether a correction for misalignment accurately accounts for sample motion.

14 Claims, 9 Drawing Sheets

DETERMINE MISALIGNMENT CORRECTION FOR IMAGE j

VALIDATE MISALIGNMENT CORRECTION FOR IMAGE j

Hamming + LOG 9

FIG. 6C

Feathering + LOG 9

FIG. 6D

Feathering + LOG 21

FIG. 6E

Feathering + LOG 31

FIG. 6F

METHODS AND SYSTEMS FOR CORRECTING IMAGE MISALIGNMENT

PRIOR APPLICATIONS

The present application is a divisional of U.S. patent application Ser. No. 10/273,511, filed Oct. 18, 2002, which is a continuation-in-part of U.S. patent application Ser. No. 10/068,133, filed Feb. 5, 2002, which is a continuation of U.S. patent application Ser. No. 09/738,614, filed Dec. 15, 2000, which claims priority to and the benefit of U.S. Provisional Patent Application Ser. No. 60/170,972, filed Dec. 15, 1999. The parent application, U.S. patent application Ser. No. 10/273,511, also claims the benefit of U.S. Provisional Patent Application No. 60/414,767, filed on Sep. 30, 2002. All of the above applications are assigned to the common assignee of this application and are hereby incorporated by reference.

FIELD OF THE INVENTION

This invention relates generally to image processing. More particularly, the invention relates to correcting image misalignment, where the misalignment is due at least in part to sample movement.

BACKGROUND OF THE INVENTION

In modern medical practice, it is useful to analyze a sequence of images of in vivo tissue obtained throughout the course of a diagnostic medical procedure. For example, in screening for some forms of cervical cancer, a chemical agent is applied to cervical tissue and the optical response of the tissue is captured in a sequence of colposcopic images. The tissue is characterized by analyzing the time-dependent response of the tissue, as recorded in the sequence of images. During this type of diagnostic procedure, the tissue may move while images are being taken, resulting in a spatial shift of the tissue within the image frame field. The tissue movement may be caused by the natural movement of the patient during the procedure, which can occur even though the patient attempts to remain completely still. Accurate analysis of the sequence of images may require that the images be adjusted prior to analysis to compensate for misalignment caused at least in part by patient movement.

There is currently a method of stabilizing an electronic image by generating a motion vector which represents the amount and direction of motion occurring between consecutive frames of a video signal. See U.S. Pat. No. 5,289,274 to Kondo. However, this method accounts for certain gross movements of a video camera—in particular, certain vibrations caused by the operator of a handheld camcorder. The method does not compensate for misalignment caused by movement of a sample. For example, such a method could not be used to adequately correct an image misalignment caused by the small-scale movement of a patient during a diagnostic procedure.

Another image stabilization method is based on detecting the physical movement of the camera itself. See U.S. Pat. No. 5,253,071 to MacKay, which describes the use of a gimbaled ring assembly that moves as a camera is physically jittered. These types of methods cannot be used to correct misalignments caused by the movement of a sample.

SUMMARY OF THE INVENTION

The invention provides methods of correcting misalignments between sequential images of a sample. The invention is particularly useful for correcting image misalignment due to movement of the sample between images and/or during image acquisition. The invention also allows for real-time, dynamic image alignment for improved optical diagnosis and assessment.

In a preferred embodiment, the invention comprises determining an x-displacement and a y-displacement corresponding to a misalignment between two images of a tissue sample, where the misalignment is caused by a shift in the position of the sample with respect to the image frame field. For example, in obtaining a sequence of images of an in-situ tissue sample, an embodiment of the invention makes it possible to correct for small image misalignments caused by unavoidable patient motion, such as motion due to breathing. It has been discovered that validating misalignment corrections improves the accuracy of diagnostic procedures that use data from sequential images, particularly where the misalignments are small and the need for accuracy is great. Thus, methods of the invention comprise validating misalignment corrections by splitting individual images into smaller subimages, determining displacement between these subimages, and comparing the subimage displacements to the overall image displacement. Alternatively, validation may comprise adjusting two images according to a misalignment correction, then determining displacement between corresponding subimages and comparing these displacements with a threshold maximum value.

It has also been discovered that application of a chemical contrast agent, such as acetic acid, prior to or during acquisition of a sequence of tissue images enhances the detection of small-scale image misalignment by increasing intra-image contrast of the tissue images. The enhanced contrast of the tissue features recorded in the images allows for more accurate motion correction determination, since enhanced features may serve as landmarks in determining values of displacement.

Both misalignment correction determination and validation may be performed such that an accurate adjustment is made for a misalignment before an entire sequence of images is obtained. This allows, for example, "on the fly" adjustment of a camera while a diagnostic exam is in progress. Thus, corrections may be determined, validated, and accurately adjusted for as misalignments occur, reducing the need for retakes and providing immediate feedback as to whether an examination is erroneous. Automatic adjustment may be accomplished by adjusting aspects of the optical interrogation of the sample using a misalignment correction value. Adjustments may be performed, for example, by adjusting aspects of transmission and/or reception of electromagnetic energy associated with the sample. This may include, for example, transmitting a correction signal to a galvanometer system or a voice coil to "null out" a misalignment by adjusting the position of a mirror or other component of the camera obtaining the images according to the correction signal. Alternatively, or additionally, adjustments may be performed by electronically adjusting an aspect of an image, for example, the frame and/or bounds of an image, according to a misalignment correction value, or by performing any other appropriate adjustment procedure.

Applications of methods of the invention include the processing and analysis of a sequence of images of biological tissue. For example, chemical agents are often applied to tissue prior to optical measurement in order to elucidate physiological properties of the tissue. In one embodiment, acetic acid is applied to cervical tissue in order to whiten the tissue in a way that allows enhanced optical discrimination between normal tissue and certain kinds of diseased tissue.

The acetowhitening technique, as well as other diagnostic techniques, and the analysis of images and spectral data obtained during acetowhitening tests are described in co-owned U.S. patent application Ser. No. 10/099,881, filed Mar. 15, 2002, and co-owned U.S. patent application entitled, "Method and Apparatus for Identifying Spectral Artifacts," identified by Ser. No. 10/243,535, filed Sep. 13, 2002, both of which are hereby incorporated by reference.

A typical misalignment between two images is less than about 0.55-mm within a two-dimensional, 480×500 pixel image frame field covering an area of approximately 25-mm× 25-mm. These dimensions provide an example of the relative scale of misalignment versus image size. In some instances it is only necessary to compensate for misalignments of less than about one millimeter within the exemplary image frame field defined above. In other cases, it is necessary to compensate for misalignments of less than about 0.3-mm within the exemplary image frame field above. Also, the dimensions represented by the image frame field, the number of pixels of the image frame field, and/or the pixel resolution may differ from the values shown above.

A misalignment correction determination may be inaccurate, for example, due to any one or a combination of the following: non-translational sample motion such as rotational motion, local deformation, and/or warping; changing features of a sample such as whitening of tissue; and image recording problems such as focus adjustment, missing images, blurred or distorted images, low signal-to-noise ratio, and computational artifacts. Validation procedures of the invention identify such inaccuracies. The methods of validation may be conducted "on-the-fly" in concert with the methods of determining misalignment corrections in order to improve accuracy and to reduce the time required to conduct a given test.

Once an image misalignment is detected, an embodiment provides for automatically adjusting an optical signal detection device, such as a camera. For example, a camera may be adjusted "on-the-fly" to compensate for misalignments as images are obtained. This improves accuracy and reduces the time required to conduct a given test.

The optical signal detection device comprises a camera, a spectrometer, or any other device which detects optical signals. The optical signal may be emitted by the sample, diffusely reflected by the sample, transmitted through the sample, or otherwise conveyed from the sample. The optical signal comprises light of wavelength falling in a range between about 190-nm and about 1100-nm. One embodiment comprises obtaining one or more of the following from one or more regions of the tissue sample: fluorescence spectral data, reflectance spectral data, and video images.

Methods comprise analysis of a sample of human tissue, such as cervical tissue. Methods of the invention also include analysis of other types of tissue, such as non-cervical tissue and/or nonhuman tissue. For example, methods comprise analysis of one or more of the following types of tissue: colorectal, gastroesophageal, urinary bladder, lung, skin, and any other tissue type comprising epithelial cells.

A common source of misalignment is movement of a sample. Methods comprise the steps of: obtaining a plurality of sequential images of a sample using an optical signal detection device; determining a correction for a misalignment between two or more of the sequential images, where the misalignment is due at least in part to a movement of the sample; and compensating for the misalignment by automatically adjusting the optical signal detection device.

The two or more sequential images may be consecutive, or they may be nonconsecutive. In one embodiment, a misalignment correction is identified between a first image and a second image, where the second image is subsequent to the first image. The first image and second image may be either consecutive or nonconsecutive.

Identifying a misalignment correction may involve data filtering. For example, some methods comprise filtering a subset of data from a first image of a plurality of sequential images. A variety of data filtering techniques may be used. In one embodiment, Laplacian of Gaussian filtering is performed. Identifying a misalignment may comprise preprocessing a subset of data from the first image prior to filtering. For example, color intensities may be converted to gray scale before filtering. In some embodiments, filtering comprises frequency domain filtering and/or discrete convolution in the space domain.

In order to identify a correction for a misalignment, preferred embodiments comprise computing a cross correlation using data from each of two of the plurality of sequential images. In some embodiments, computing a cross correlation comprises computing a product represented by $F_i(u,v) F^*_j(u,v)$, where $F_i(u,v)$ is a Fourier transform of data derived from a subset of data from a first image, i, of the plurality of sequential images, $F^*_j(u,v)$ is a complex conjugate of a Fourier transform of data derived from a subset of data from a second image, j, of the plurality of sequential images, and u and v are frequency domain variables. In preferred embodiments, the computing of the cross correlation additionally comprises computing an inverse Fourier transform of the product represented by $F_i(u,v) F^*_j(u,v)$.

A method of the invention comprises validating a correction for a misalignment determined between a first image and a second image. Validating a misalignment correction comprises defining one or more validation cells within a bounded image plane; computing for each validation cell a measure of displacement between two (or more) images bound by the image plane using data from the two images corresponding to each validation cell; and validating a correction for misalignment between the two images by comparing the validation cell displacements with the correction. Preferably, each validation cell comprises a subset of the bounded image plane. The two (or more) images may be consecutive images. In some embodiments, the validating step includes eliminating from consideration one or more measures of displacement for corresponding validation cells. For example, measures of displacement from validation cells determined to be likely to contribute to an erroneous validation result are eliminated in some embodiments. In some embodiments, identifying validation cells that are likely to contribute to an erroneous validation result comprises calculating a sum squared gradient for at least one validation cell.

Methods of the invention comprise obtaining a plurality of sequential images of the sample during an application of a chemical agent to the sample. For example, the chemical agent comprises at least one of the following: acetic acid, formic acid, propionic acid, butyric acid, Lugol's iodine, Shiller's iodine, methylene blue, toluidine blue, indigo carmine, indocyanine green, and fluorescein. Some embodiments comprise obtaining sequential images of the sample during an acetowhitening test.

In preferred embodiments, the movement of the sample is relative to the optical signal detection device and comprises at least one of the following: translational motion, rotational motion, warping, and local deformation.

One or more of the sequential images comprise measurements of an optical signal from the sample. The optical signal comprises, for example, visible light, fluoresced light, and/or another form of electromagnetic radiation.

Methods of the invention comprise determining a correction for misalignment between each of a plurality of pairs of images. Such methods comprise the steps of: obtaining a set of sequential images of a sample using an optical signal detection device; and determining a correction for a misalignment between each of a plurality of pairs of the sequential images, where at least one of the misalignments is due at least in part to a movement of the sample. The correction may then be used to compensate for each of the misalignments by automatically adjusting the optical signal detection device.

The obtaining step and the determining step may be performed alternately or concurrently, for example. One embodiment comprises determining a correction for a misalignment between a pair of the sequential images less than about 2 seconds after obtaining the latter of the pair of the sequential images. In another embodiment, this takes less than about one second.

In another aspect, the invention is directed to a method of determining a correction for a misalignment that includes validating the correction. Methods comprise the steps of: obtaining a plurality of sequential images of a sample using an optical signal detection device; determining a correction for a misalignment between at least two of the sequential images; and validating the correction for misalignment between two of the images. An embodiment further comprises compensating for the misalignment by automatically adjusting the optical signal detection device according to the correction determined. In one embodiment, determining a misalignment correction between two images and validating the correction is performed in less than about one second.

Methods of the invention comprise compensating for a misalignment by determining a correction for a misalignment between a pair of images, validating the misalignment, and automatically realigning one of the pair of images. The realignment may be performed during the acquisition of the images, or afterwards.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views.

FIG. 2B is divided into FIG. 2B-1 and FIG. 2B-2.

FIG. 2C is divided into FIG. 2C-1 and FIG. 2C-2.

DESCRIPTION OF THE ILLUSTRATIVE EMBODIMENT

In general, the invention provides methods of determining a correction for a misalignment between images in a sequence due to movement of a sample. These methods are useful, for example, in the preparation of a sequence of images for analysis, as in medical diagnostics.

In some diagnostic procedures, methods of the invention comprise applying an agent to a tissue in order to change its optical properties in a way that is indicative of the physiological state of the tissue. The rate and manner in which the tissue changes are important in the characterization of the tissue.

Certain embodiments of the invention comprise automated and semi-automated analysis of diagnostic procedures that have traditionally required analysis by trained medical personnel. Diagnostic procedures which use automatic image-based tissue analysis provide results having increased sensitivity and/or specificity. See, e.g., co-owned U.S. patent application Ser. No. 10/099,881, filed Mar. 15, 2002, and co-owned U.S. patent application entitled, "Method and Apparatus for Identifying Spectral Artifacts," identified by Ser. No. 10/243,535, filed Sep. 13, 2002, both of which are incorporated herein by reference.

In order to facilitate such automatic analysis, it is often necessary to adjust for misalignments caused by sample movement that occurs during the diagnostic procedure. For example, during a given procedure, in vivo tissue may spatially shift within the image frame field from one image to the next due to movement of the patient. Accurate diagnosis requires that this movement be taken into account in the automated analysis of the tissue sample. In some exemplary embodiments, spatial shift correction made at the time images are obtained is more accurate than correction made after all the images are obtained, since "on-the-fly" corrections compensate for smaller shifts occurring over shorter periods of time, rather than larger, more cumulative shifts occurring over longer periods of time.

If a sample moves while a sequence of images is obtained, the procedure may have to be repeated. For example, this may be because the shift between consecutive images is too large to be accurately compensated for, or because a region of interest moves outside of a usable portion of the frame captured by the optical signal detection device. It is often preferable to compensate for misalignments resulting from sample movement during the collection of images rather than wait until the entire sequence of images has been obtained before compensating for misalignments. Stepwise adjustment of an optical signal detection device throughout image capture reduces the cumulative effect of sample movement. If adjustment is made only after an entire sequence is obtained, it may not be possible to accurately compensate for some types of sample movement. On-the-fly, stepwise compensation for misalignment reduces the need for retakes.

On-the-fly compensation may also obviate the need to obtain an entire sequence of images before making the decision to abort a failed procedure, particularly when coupled with on-the-fly, stepwise validation of the misalignment correction determination. For example, if the validation procedure detects that a misalignment correction determination is either too large for adequate compensation to be made or is invalid, the procedure may be aborted before obtaining the entire sequence of images. It can be immediately determined whether or not the obtained data is useable. Retakes may be performed during the same patient visit; no follow-up visit to repeat an erroneous test is required. A diagnostic test invalidated by excessive movement of the patient may be aborted before obtaining the entire sequence of images.

In preferred embodiments, a determination of misalignment correction is expressed as a translational displacement in two dimensions, x and y. Here, x and y represent Cartesian coordinates indicating displacement on the image frame field plane. In other embodiments, corrections for misalignment are expressed in terms of non-Cartesian coordinate systems, such as biradical, spherical, and cylindrical coordinate systems, among others. Alternatives to Cartesian-coordinate systems may be useful, for example, where the image frame field is non-planar.

Some types of sample motion—including rotational motion, warping, and local deformation—may result in an invalid misalignment correction determination, since it may be impossible to express certain instances of these types of sample motion in terms of a translational displacement, for example, in the two Cartesian coordinates x and y. It is noted, however, that in some embodiments, rotational motion, warping, local deformation, and/or other kinds of non-translational motion are acceptably accounted for by a correction expressed in terms of a translational displacement. The changing features of the tissue, as in acetowhitening, may also affect the determination of a misalignment correction. Image recording problems such as focus adjustment, missing images, blurred or distorted images, low signal-to-noise ratio (i.e. caused by glare), and computational artifacts may affect the correction determination as well. Therefore, validation of a determined correction is often required. In some embodiments, a validation step includes determining whether an individual correction for misalignment is erroneous, as well as determining whether to abort or continue the test in progress. Generally, validation comprises splitting at least a portion of each of a pair of images into smaller, corresponding units (subimages), determining for each of these smaller units a measure of the displacement that occurs within the unit between the two images, and comparing the unit displacements to the overall displacement between the two images.

In certain embodiments, the method of validation takes into account the fact that features of a tissue sample may change during the capture of a sequence of images. For example, the optical intensity of certain regions of tissue change during an acetowhitening test. Therefore, in preferred embodiments, validation of a misalignment correction determination is performed using a pair of consecutive images. In this way, the difference between the corresponding validation cells of the two consecutive images is less affected by gradual tissue whitening changes, as compared with images obtained further apart in time. In some embodiments, validation is performed using pairs of nonconsecutive images taken within a relatively short period of time, compared with the time in which the overall sequence of images is obtained. In other embodiments, validation comprises the use of any two images in the sequence of images.

In some exemplary embodiments, a determination of misalignment correction between two images may be inadequate if significant portions of the images are featureless or have low signal-to-noise ratio (i.e. are affected by glare). Similarly, validation using cells containing significant portions which are featureless or which have low signal-to-noise ratio may result in the erroneous invalidation of valid misalignment correction determinations in cases where the featureless portion of the overall image is small enough so that it does not adversely affect the misalignment correction determination. For example, analysis of featureless validation cells may produce meaningless correlation coefficients. One embodiment comprises identifying one or more featureless cells and eliminating them from consideration in the validation of a misalignment correction determination, thereby preventing rejection of a good misalignment correction.

A determination of misalignment correction may be erroneous due to a computational artifact of data filtering at the image borders. For example, in one exemplary embodiment, an image with large intensity differences between the upper and lower borders and/or the left and right borders of the image frame field undergoes Laplacian of Gaussian frequency domain filtering. Since Laplacian of Gaussian frequency domain filtering corresponds to cyclic convolution in the space-time domain, these intensity differences (discontinuities) yield a large gradient value at the image border, and cause the overall misalignment correction determination to be erroneous, since changes between the two images due to spatial shift are dwarfed by the edge effects. Certain embodiments employ pre-multiplication of image data by a Hamming window to remove or reduce this "wraparound error." Preferred embodiments employ image-blending techniques such as feathering, to smooth any border discontinuity, while requiring only a minimal amount of additional processing time.

Figure 1A:
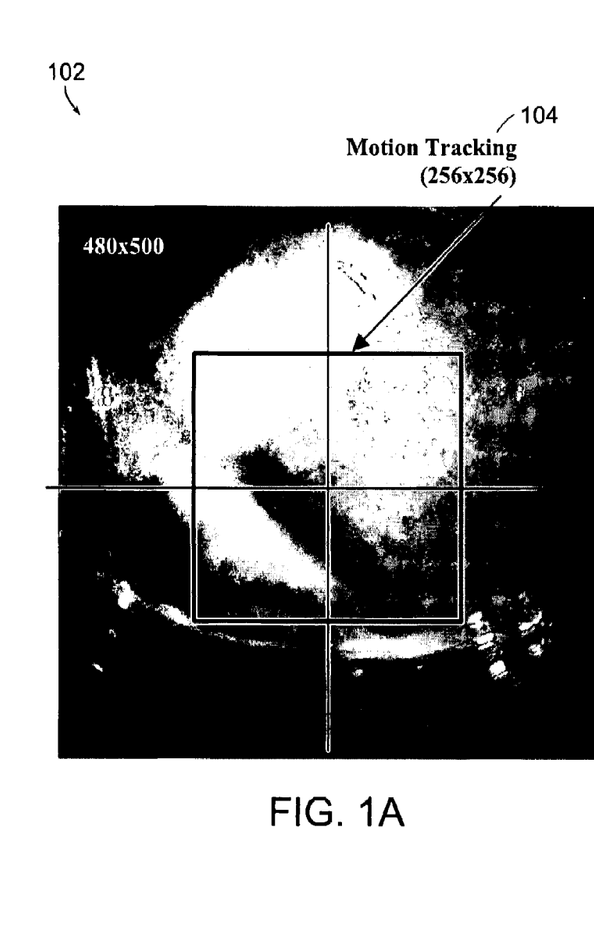
FIG. 1A represents a 480×500 pixel image from a sequence of images of in vivo human cervix tissue and shows a 256×256 pixel portion of the image from which data is used in determining a correction for a misalignment between two images from a sequence of images of the tissue according to an illustrative embodiment of the invention.

FIG. 1A represents a 480×500 pixel image 102 from a sequence of images of in vivo human cervix tissue and shows a 256×256 pixel portion 104 of the image from which data is used in identifying a misalignment correction between two images from a sequence of images of the tissue, according to an illustrative embodiment of the invention. Preferred embodiments comprise illuminating the tissue using either or both a white light source and a UV light source. The image 102 of FIG. 1A has a pixel resolution of about 0.054-mm. The embodiments described herein show images with pixel resolutions of about 0.0547-mm to about 0.0537-mm. Other embodiments have pixel resolutions outside this range. In some embodiments, the images of a sequence have an average pixel resolution of between about 0.044-mm and about 0.064-mm. In the embodiment of FIG. 1A, the central 256×256 pixels 104 of the image 102 are chosen for use in motion tracking. Other embodiments use regions of different sizes for motion tracking, and these regions are not necessarily located in the center of the image frame field. In the embodiment of FIG. 1A, the method of motion tracking determines an x-displacement and a y-displacement corresponding to the translational shift (misalignment) between the 256×256 central portions 104 of two images in the sequence of images.

Figure 1B:
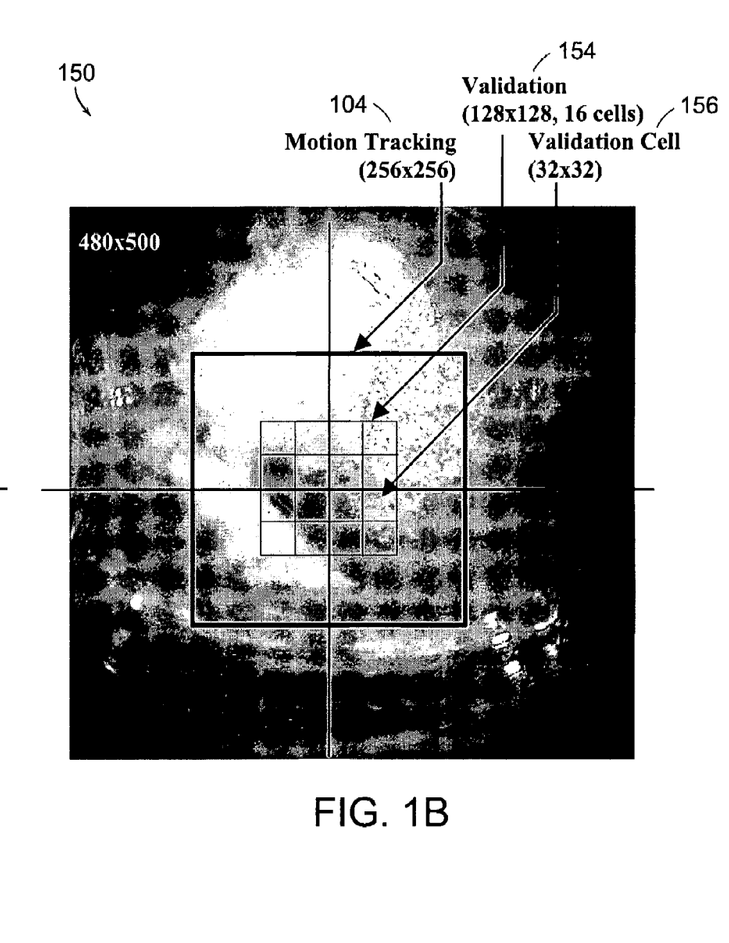
FIG. 1B depicts the image represented in FIG. 1A and shows a 128×128 pixel portion of the image, made up of 16 individual 32×32 pixel validation cells, from which data is used in performing a validation of the misalignment correction determination according to an illustrative embodiment of the invention.

The determination of misalignment correction may be erroneous for any number of various reasons, including but not limited to non-translational sample motion (i.e. rotational motion, local deformation, and/or warping), changing features of a sample (i.e. whitening of tissue), and image recording problems such as focus adjustment, missing images, blurred or distorted images, low signal-to-noise ratio, and computational artifacts. Therefore, in preferred embodiments, validation comprises splitting an image into smaller units (called cells), determining displacements of these cells, and comparing the cell displacements to the overall displacement. FIG. 1B depicts the image represented in FIG. 1A and shows a 128×128 pixel portion 154 of the image, made up of 16 individual 32×32 pixel validation cells 156, from which data is used in performing a validation of the misalignment correction, according to an illustrative embodiment of the invention.

Figure 2A:
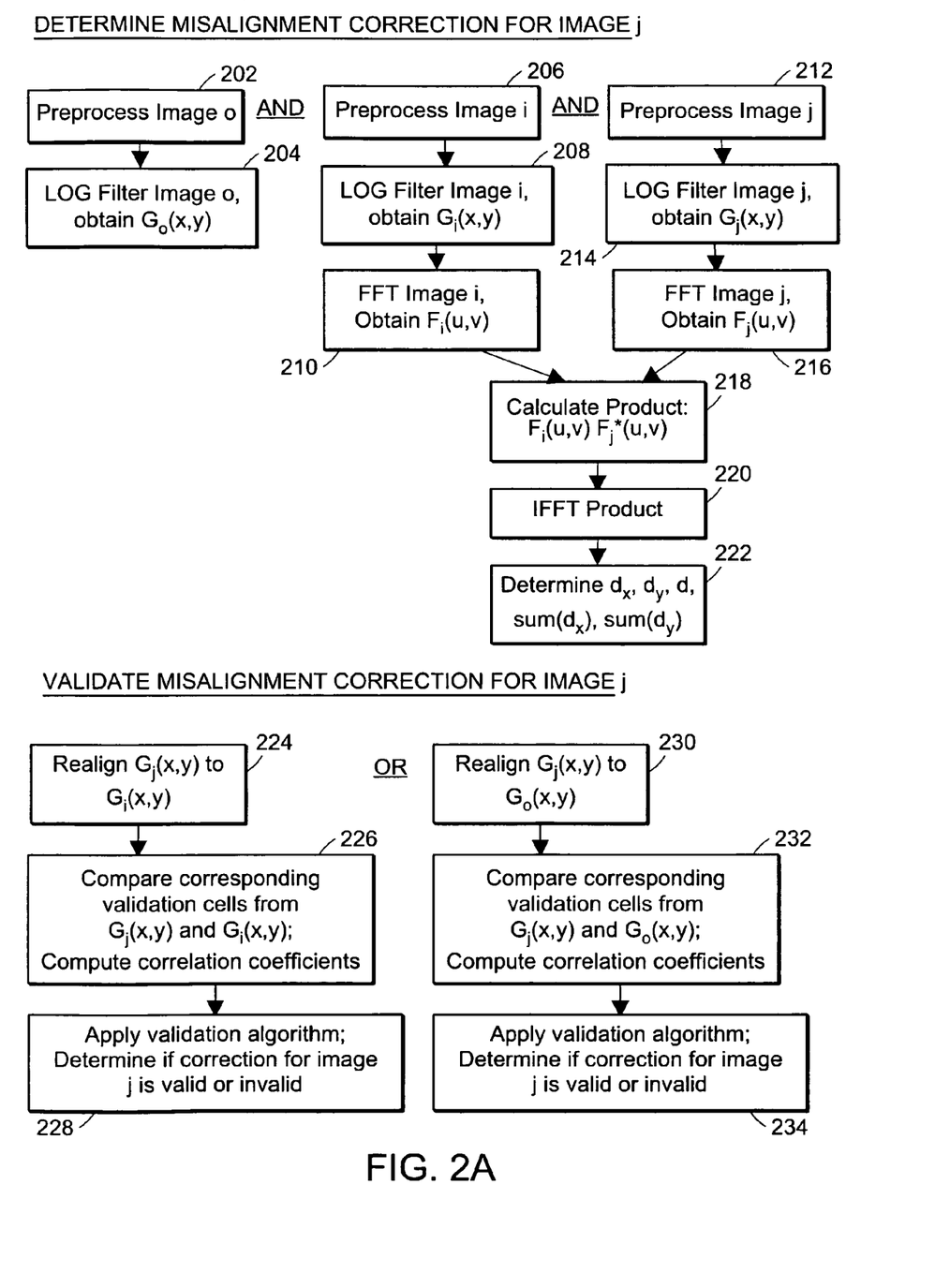
FIG. 2A is a schematic flow diagram depicting steps in a method of determining a correction for a misalignment between two images due to at least in part to the movement of a sample according to an illustrative embodiment of the invention.
Figures 2B, 2B:
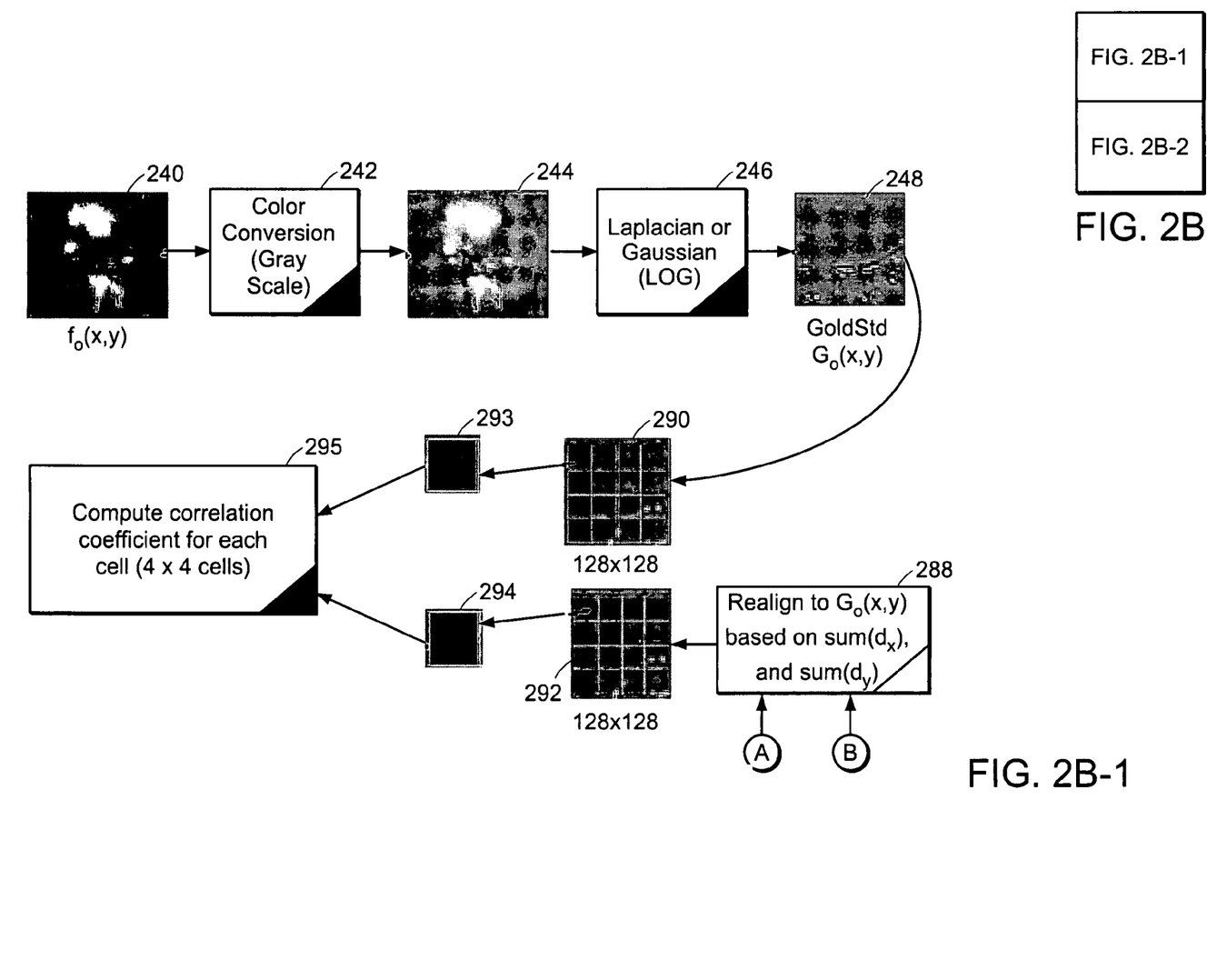
FIG. 2B is a schematic flow diagram depicting steps in a version of the method shown in FIG. 2A of determining a correction for a misalignment between two images due to at least in part to the movement of a sample according to an illustrative embodiment of the invention.
Figure 2B:
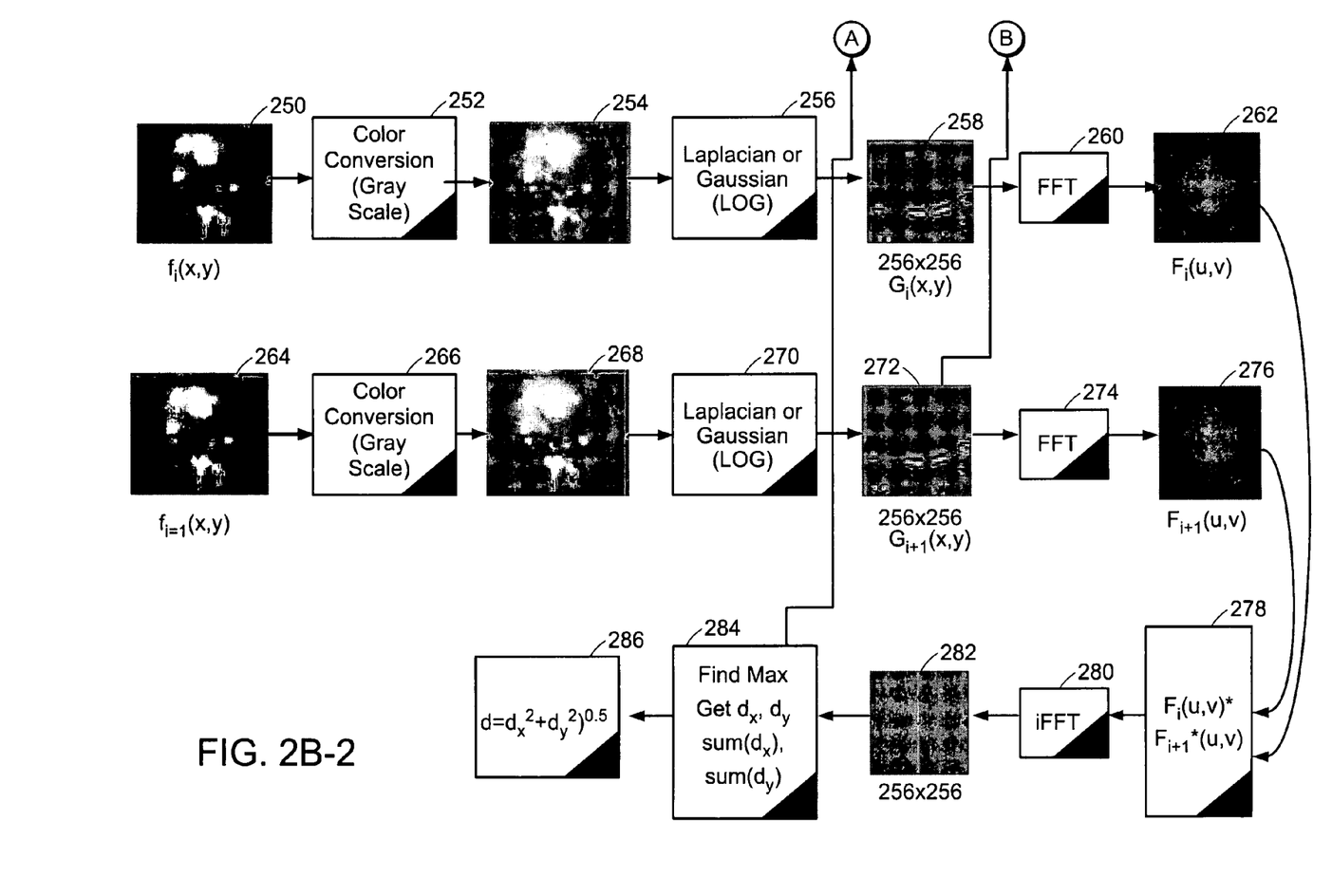
FIG. 2C is a schematic flow diagram depicting steps in a version of the method shown in FIG. 2A of determining a correction for a misalignment between two images due to at least in part to the movement of a sample according to an illustrative embodiment of the invention.
Figures 2C, 2C:
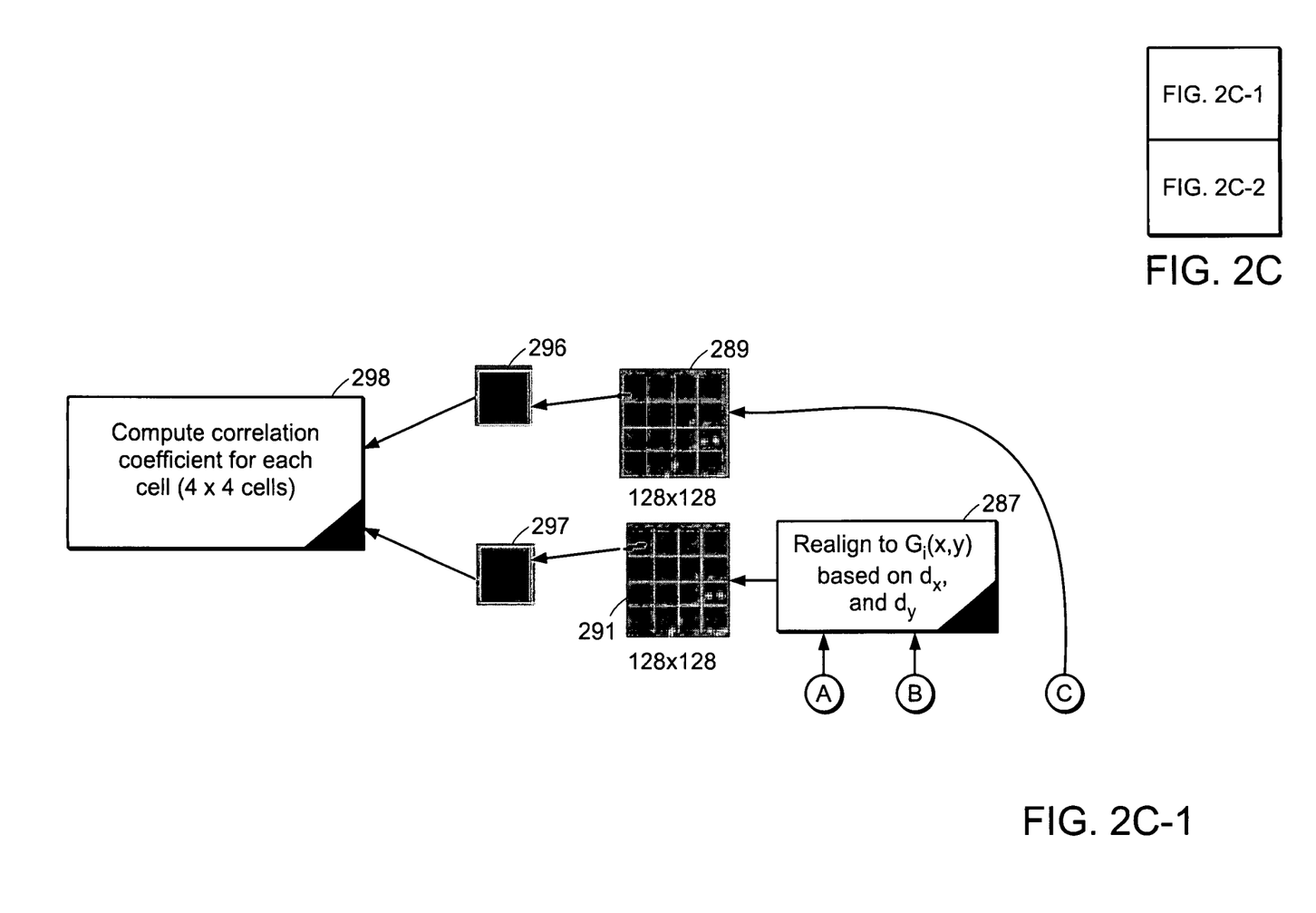
Figure 2C:
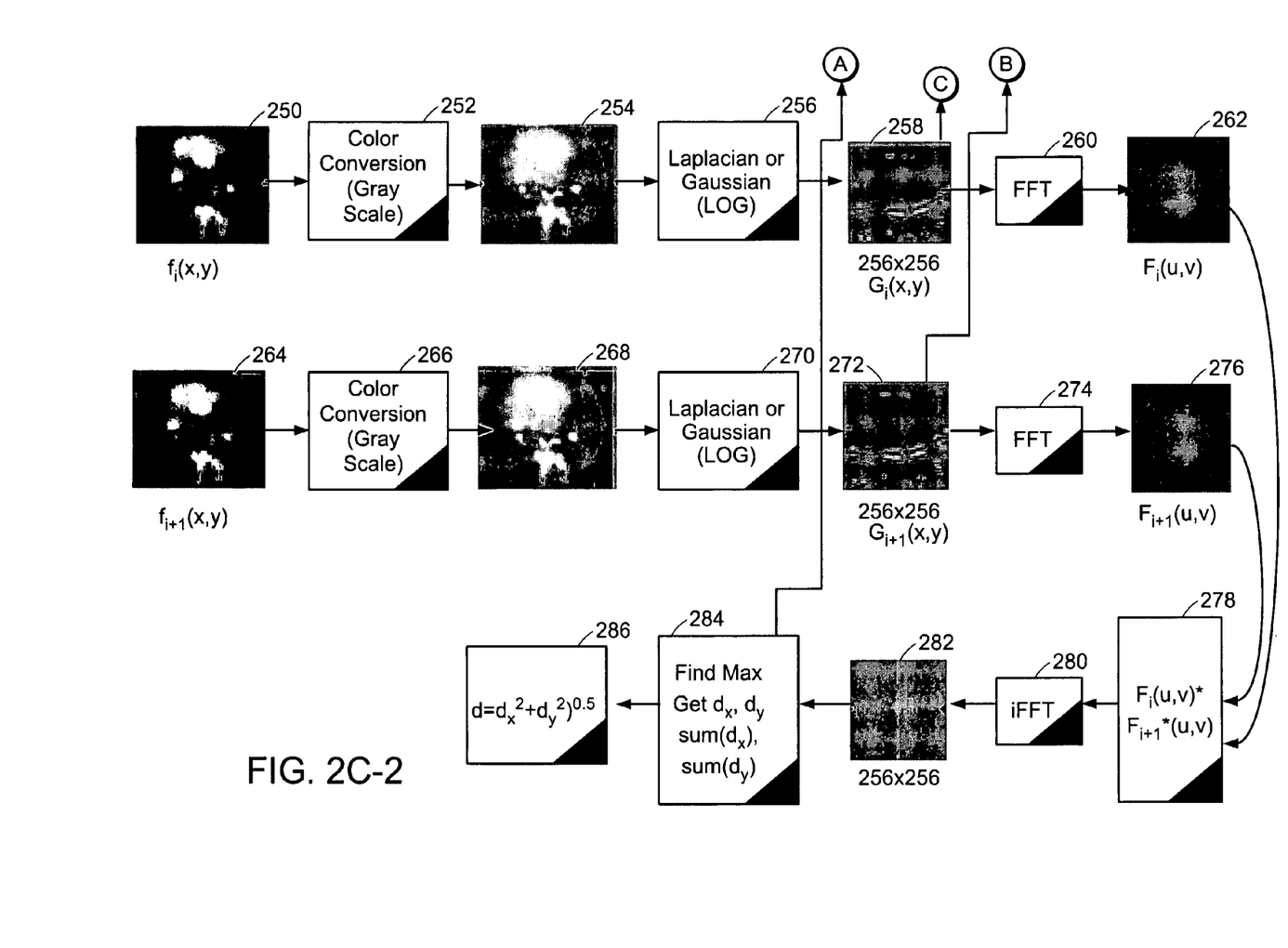
Figure 3A:
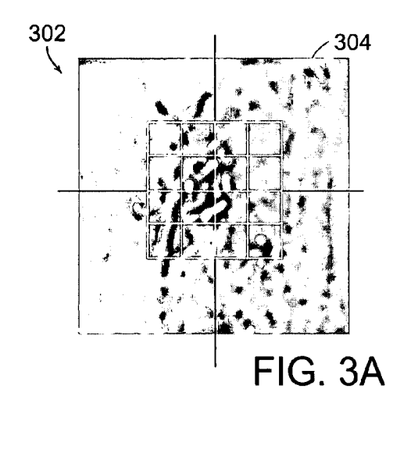
FIGS. 3A-3F depicts a subset of adjusted images from a sequence of images of a tissue with an overlay of gridlines showing the validation cells used in validating the determinations of misalignment correction between the images according to an illustrative embodiment of the invention.
Figure 3B:
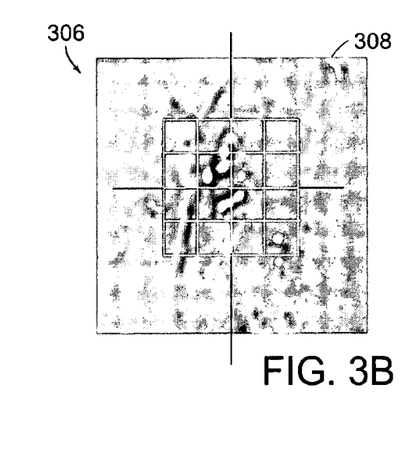
Figure 3C:
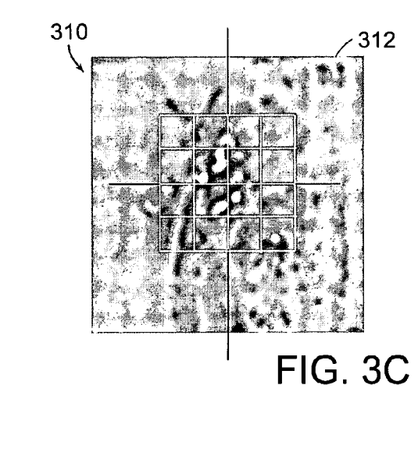
Figure 3D:
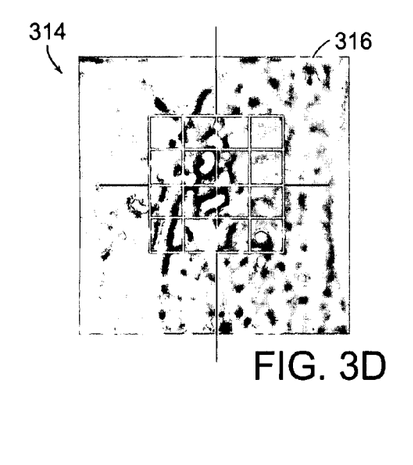
Figure 3E:
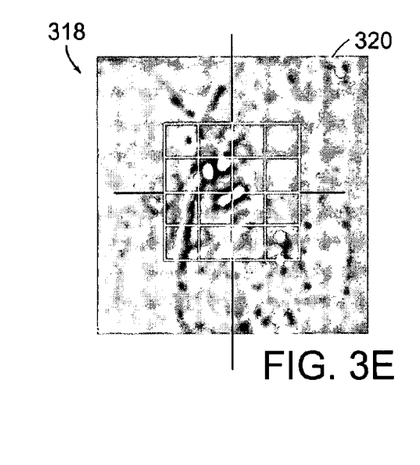
Figure 3F:
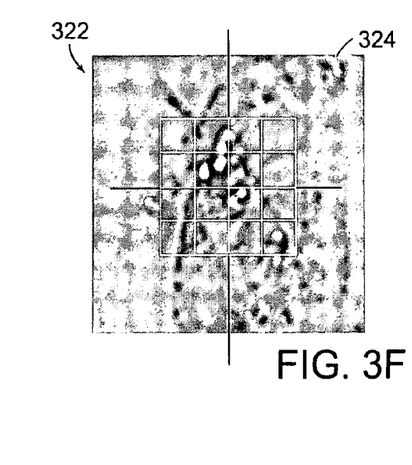

FIG. 2A, FIG. 2B, and FIG. 2C depict steps in illustrative embodiment methods of determining a misalignment correction between two images of a sequence, and methods of validating that determination. Steps 202 and 204 of FIG. 2A depict steps of developing data from an initial image with which data from a subsequent image are compared in order to determine a misalignment correction between the subsequent image and the initial image. An initial image "o" is preprocessed 202 then filtered 204 to obtain a matrix of values, for example, optical intensities, representing a portion of the initial image. In one embodiment, preprocessing includes transforming the three RGB color components into a single intensity component. An exemplary intensity component is CCIR 601, shown in Equation 1:

$$I = 0.299R + 0.587G + 0.114B \tag{1}$$

where I is the CCIR 601 "gray scale" intensity component, expressed in terms of red (R), green (G), and blue (B) intensities. CCIR 601 intensity may be used, for example, as a measure of the "whiteness" of a particular pixel in an image from an acetowhitening test. Different expressions for intensity may be used, and the choice may be geared to the specific type of diagnostic test conducted. In an alternative embodiment, a measure of radiant power as determined by a spectrometer may be used in place of the intensity component of Equation (1). Some embodiments comprise obtaining multiple types of optical signals simultaneously or contemporaneously; for example, some embodiments comprise obtaining a. combination of two or more of the following signals: fluorescence spectra, reflectance (backscatter) spectra, and a video signal. Step 202 of FIG. 2A is illustrated in blocks 240, 242, and 244 of FIG. 2B, where block 240 represents the initial color image, "o", in the sequence, block 242 represents conversion of color data to gray scale using Equation 1, and block 244 represents the image of block 240 after conversion to gray scale.

Step 204 of FIG. 2A represents filtering a 256×256 portion of the initial image, for example, a portion analogous to the 256×256 central portion 104 of the image 102 of FIG. 1A, using Laplacian of Gaussian filtering. Other filtering techniques are used in other embodiments. Preferred embodiments employ Laplacian of Gaussian filtering, which combines the Laplacian second derivative approximation with the Gaussian smoothing filter to reduce the high frequency noise components prior to differentiation. This filtering step may be performed by discrete convolution in the space domain, or by frequency domain filtering. The Laplacian of Gaussian (LoG) filter may be expressed in terms of x and y coordinates (centered on zero) as shown in Equation (2):

$$LoG(x, y) = -\frac{1}{\pi\sigma^4}\left[1 - \frac{x^2 + y^2}{2\sigma^2}\right]e^{-\frac{x^2+y^2}{2\sigma^2}} \tag{2}$$

where x and y are space coordinates and σ is the Gaussian standard deviation. In one preferred embodiment, an approximation to the LoG function is used. In the embodiments described herein, approximation kernels of size 9×9, 21×21, and 31×31 are used. The Gaussian standard deviation σ a is chosen in certain preferred embodiments as shown in Equation (3):

$$\sigma = LoG\ filter\ size\ /8.49 \tag{3}$$

where LoG filter size corresponds to the size of the discrete kernel approximation to the LoG function (i.e. 9, 21, and 31 for the approximation kernels used herein). Other embodiments employ different kernel approximations and/or different values of Gaussian standard deviation.

The LoG filter size may be chosen so that invalid scans are failed and valid scans are passed with a minimum of error. Generally, use of a larger filter size is better at reducing large structured noise and is more sensitive to larger image features and larger motion, while use of a smaller filter size is more sensitive to smaller features and smaller motion. One embodiment of the invention comprises using more than one filter size, adjusting to coordinate with the kind of motion being tracked and the features being imaged.

Step 204 of FIG. 2A is illustrated in FIG. 2B in blocks 244, 246, and 248, where block 244 represents data from the initial image in the sequence after conversion to gray scale intensity, block 246 represents the application of the LoG filter, and block 248 represents the 256×256 matrix of data values, $G_o(x,y)$, which is the "gold standard" by which other images are compared in validating misalignment correction determinations in this embodiment. As detailed in FIG. 2C, preferred embodiments validate a misalignment correction determination by comparing a given image to its preceding image in the sequence, not by comparing a given image to the initial image in the sequence as shown in FIG. 2B. Although FIG. 2A, FIG. 2B, and FIG. 2C show application of the LoG filter as a discrete convolution in the space domain, resulting in a standard expressed in space coordinates, other preferred embodiments comprise applying the LoG filter in the frequency domain. In either case, the LoG filter is preferably zero padded to the image size.

Steps 206 and 208 of FIG. 2A represent preprocessing an image "i", for example, by converting RGB values to gray scale intensity as discussed above, and performing LoG filtering to obtain $G_i(x,y)$, a matrix of values from image "i" which is compared with that of another image in the sequence in order to determine a misalignment correction between the two images. Steps 206 and 208 of FIG. 2A are illustrated in FIG. 2B in blocks 250, 252, 254, 256, and 258, where $f_i(x,y)$ in block 250 is the raw image data from image "i", block 252 represents conversion of the $f_i(x,y)$ data to gray scale intensities as shown in block 254, and block 256 represents application of the LoG filter on the data of block 254 to produce the data of block 258, $G_i(x,y)$.

Similarly, steps 212 and 214 of FIG. 2A represent preprocessing an image "j", for example, by converting RGB values to gray scale intensity as discussed above, and performing LoG filtering to obtain $G_j(x,y)$, a matrix of values from image "j", with is compared with image "i" in order to determine a measure of misalignment between the two images. In some preferred embodiments, image "j" is subsequent to image "i" in the sequence. In some preferred embodiments, "i" and "j" are consecutive images. Steps 212 and 214 of FIG. 2A are illustrated in FIG. 2B in blocks 264, 266, 268, 270, and 272, where "j" is "i+1", the image consecutive to image "i" in the sequence. In FIG. 2B, block 264 is the raw "i+1" image data, block 266 represents conversion of the "i+1" data to gray scale intensities as shown in block 268, and block 270 represents application of the LoG filter on the data of block 268 to produce the data of block 272, $G_{i+1}(x,y)$.

Steps 210 and 216 of FIG. 2A represent applying a Fourier transform, for example, a Fast Fourier Transform (FFT), using $G_i(x,y)$ and $G_j(x,y)$, respectively, to obtain $F_i(u,v)$ and $F_j(u,v)$, which are matrices of values in the frequency domain corresponding to data from images "i" and "j", respectively. Steps 210 and 216 of FIG. 2A are illustrated in FIG. 2B by blocks 258, 260, 262, 272, 274, and 276, where "j" is "i+1", the image consecutive to image "i" in the sequence. In FIG. 2B, block 258 represents the LoG filtered data, $G_i(x,y)$, corresponding to image "i", and block 260 represents taking the Fast Fourier Transform of $G_i(x,y)$ to obtain $F_i(u,v)$, shown in block 262. Similarly, in FIG. 2B block 272 is the LoG filtered data, $G_{i+1}(x,y)$, corresponding to image "i+1", and block 274 represents taking the Fast Fourier Transform of $G_{i+1}(x,y)$ to obtain $F_{i+1}(u,v)$, shown in block 276.

Step 218 of FIG. 2A represents computing the cross correlation $F_i(u,v) F^*_j(u,v)$, where $F_i(u,v)$ is the Fourier transform of data from image "i", $F^*_j(u,v)$ is the complex conjugate of the Fourier transform of data from image "j", and u and v are frequency domain variables. The cross-correlation of two signals of length $N_1$ and $N_2$ provides $N_1+N_2-1$ values; therefore, to avoid aliasing problems due to under-sampling, the two signals should be padded with zeros up to $N_1+N_2-1$ samples. Step 218 of FIG. 2A is represented in FIG. 2B by blocks 262, 276, and 278. Block 278 of FIG. 2B represents computing the cross correlation, $F_i(u,v) F^*_{i+1}(u,v)$, using $F_i(u,v)$, the Fourier transform of data from image "i", and $F^*_{i+1}(u,v)$, the complex conjugate of the Fourier transform of data from image "i+1". The cross-correlation may also be expressed as c(k,l) in Equation (4):

$$c(k,l) = \Sigma\Sigma I_1(p,q)I_2(p-k,q-l) \quad (4)$$

where variables (k,l) can be thought of as the shifts in each of the x- and y-directions which are being tested in a variety of combinations to determine the best measure of misalignment between two images $I_1$ and $I_2$, and where p and q are matrix element markers.

Step 220 of FIG. 2A represents computing the inverse Fourier transform of the cross-correlation computed in step 218. Step 220 of FIG. 2A is represented in FIG. 2B by block 280. The resulting inverse Fourier transform maps how well the 256×256 portions of images "i" and "j" match up with each other given various combinations of x- and y-shifts. Generally, the normalized correlation coefficient closest to 1.0 corresponds to the x-shift and y-shift position providing the best match, and is determined from the resulting inverse Fourier transform. In a preferred embodiment, correlation coefficients are normalized by dividing matrix values by a scalar computed as the product of the square root of the (0,0) value of the $_{auto}$-correlation of each image. In this way, variations in overall brightness between the two images have a more limited effect on the correlation coefficient, so that the actual movement within the image frame field between the two images is better reflected in the misalignment determination.

Step 222 of FIG. 2A represents determining misalignment values $d_x$, $d_y$, d, sum($d_x$), sum($d_y$), and Sum($d_j$), where $d_x$ is the computed displacement between the two images "i" and "j" in the x-direction, $d_y$ is the computed displacement between the two images in the y-direction, d is the square root of the sum $d_x^2+d_y^2$ and represents an overall displacement between the two images, sum($d_x$) is the cumulative x-displacement between the current image "j" and the first image in the sequence "o", sum($d_y$) is the cumulative y-displacement between the current image "j" and the first image in the sequence "o", and Sum($d_j$) is the cumulative displacement, d, between the current image "j" and the first image in the sequence "o". Step 222 of FIG. 2A is represented in FIG. 2B by blocks 282, 284, and 286. Blocks 284 and 286 represent finding the maximum value in the data of block 282 in order to calculate $d_x$, $d_y$, d, sum($d_x$), sum($d_y$), and Sum($d_{i+1}$) as described above, where image "j" in FIG. 2A is "i+1" in FIG. 2B, the image consecutive to image "i".

Steps 224, 226, and 228 of FIG. 2A represent one method of validating the misalignment correction determined for image "j" in step 222 of FIG. 2A. This method of validating misalignment correction is represented in blocks 287, 289, 291, 296, 297, and 298 of FIG. 2C. Another method of validating a misalignment correction is represented in steps 230, 232, and 234 of FIG. 2A; and this method is represented in blocks 288, 290, 292, 293, 294, and 295 of FIG. 2B. FIG. 2C is a schematic flow diagram depicting steps in a version of the methods shown in FIG. 2A of determining a correction for a misalignment between two images in which validation is performed using data from two consecutive images. Preferred embodiments comprise using consecutive or near-consecutive images to validate a misalignment correction determination, as in FIG. 2C. Other embodiments comprise using the initial image to validate a misalignment correction determination for a given image, as in FIG. 2B.

In FIG. 2A, step 224 represents realigning $G_j(x,y)$, the LoG-filtered data from image "j", to match up with $G_i(x,y)$, the LoG-filtered data from image "i", using the misalignment values $d_x$ and $d_y$ determined in step 222. In preferred embodiments, image "j" is consecutive to image "i" in the sequence of images. Here, image "j" is image "i+1" such that $G_i(x,y)$ is aligned with $G_{i+1}(x,y)$ as shown in block 287 of FIG. 2C. Similarly, in FIG. 2A, step 230 represents realigning $G_j(x,y)$, the LoG-filtered data from image "j", to match up with $G_0(x,y)$, the LoG-filtered "gold standard" data from the initial image "o", using the displacement values sum($d_x$) and sum($d_y$) determined in step 222. Step 230 of FIG. 2A is represented in block 288 of FIG. 2B.

Step 226 of FIG. 2A represents comparing corresponding validation cells from $G_j(x,y)$ and $G_i(x,y)$ by computing correlation coefficients for each cell. This is represented schematically in FIG. 2C by blocks 289, 291, 296, 297, and 298 for the case where j=i+1. First, a 128×128 pixel central portion of the realigned $G_{i+1}(x,y)$ is selected, and the corresponding 128×128 pixel central portion of $G_i(x,y)$ is selected, as shown in blocks 289 and 291 of FIG. 2C. An exemplary 128×128 pixel validation region 154 is shown in FIG. 1B. Then, the embodiment comprises computing a correlation coefficient for each of 16 validation cells. An exemplary validation cell from each of the realigned $G_{i+1}(x,y)$ matrix 291 and $G_i(x,y)$ matrix 289 is shown in blocks 297 and 296 of FIG. 2C. The validation cells are as depicted in the 32×32 pixel divisions 156 of the 128×128 pixel validation region 154 of FIG. 1B. Different embodiments use different numbers and/or different sizes of validation cells. Correlation coefficients are computed for each of the 16 cells, as shown in block 298 of FIG. 2C. Each correlation coefficient is a normalized cross-correlation coefficient as shown in Equation (5):

$$c'(m, n) = \frac{\sum\sum I_1[p, q] \times I_2[p, q]}{\sqrt{\sum\sum I_1^2[p, q]} \sqrt{\sum\sum I_2^2[p, q]}} \quad (5)$$

where c'(m,n) is the normalized cross-correlation coefficient for the validation cell (m,n), m is an integer 1 to 4 corresponding to the column of the validation cell whose correlation coefficient is being calculated, n is an integer 1 to 4 corresponding to the row of the validation cell whose correlation coefficient is being calculated, p and q are matrix element markers, $I_1[p,q]$ are elements of the cell in column m and row n of the 128×128 portion of the realigned image shown in block 291 of FIG. 2C, and $I_2[p,q]$ are elements of the cell in column m and row n of the 128×128 portion of $G_1(x,y)$ shown in block 289 of FIG. 2C. Here, p=1 to 32 and q=1 to 32, and the sums shown in Equation (5) are performed over p and q. The cross-correlation coefficient of Equation (5) is similar to an auto-correlation in the sense that a subsequent image is realigned with a prior image based on the determined misalignment correction so that, ideally, the aligned images appear to be identical. A low value of c'(m,n) indicates a mismatching between two corresponding cells. The misalignment correction determination is then either validated or rejected based on the values of the 16 correlation coefficients computed in step 298 of FIG. 2C. For example, each correlation coefficient may be compared against a threshold maximum value. This corresponds to step 228 of FIG. 2A.

Step 232 of FIG. 2A represents comparing corresponding validation cells from $G_j(x,y)$ and $G_o(x,y)$ by computing correlation coefficients for each cell. This is represented schematically in FIG. 2B by blocks 290, 292, 293, 294, and 295 for the case where j=i+1. First, a 128×128 pixel central portion of the realigned $G_{i+1}(x,y)$ is selected, and the corresponding 128×128 pixel central portion of $G_o(x,y)$ is selected, as shown in blocks 292 and 290 of FIG. 2B. An exemplary 128×128 pixel validation region 154 is shown in FIG. 1B. Then, the embodiment comprises computing a correlation coefficient for each of the 16 validation cells. An exemplary validation cell from each of the realigned $G_{i+1}(x,y)$ matrix 292 and $G_o(x,y)$ matrix 290 is shown in blocks 294 and 293 of FIG. 2B. The validation cells are as depicted in the 32×32 pixel divisions of the 128×128 pixel validation region 154 of FIG. 1B. Different embodiments use different numbers and/or different sizes of validation cells. Correlation coefficients are computed for each of the 16 cells, as shown in block 295 of FIG. 2B. Each correlation coefficient is a normalized "auto"-correlation coefficient as shown in Equation (5) above, where $I_1[p,q]$ are elements of the cell in column m and row n of the 128×128 portion of the realigned subsequent image shown in block 292 of FIG. 2B, and $I_2[p,q]$ are elements of the cell in column m and row n of the 128×128 portion of $G_o(x,y)$ shown in block 290 of FIG. 2B. A low value of c'(m,n) indicates a mismatching between two corresponding cells. The misalignment determination is then either validated or rejected based on the values of the 16 correlation coefficients computed in step 295 of FIG. 2C. This corresponds to step 234 of FIG. 2A.

In an illustrative embodiment, determinations of misalignment correction and validation of these determinations as shown in each of FIG. 2A, FIG. 2B, and FIG. 2C are performed using a plurality of the images in a given sequence. In preferred embodiments, determinations of misalignment correction and validations thereof are performed while images are being obtained, so that an examination in which a given sequence of images is obtained may be aborted before all the images are obtained. In some embodiments, a misalignment correction is determined, validated, and compensated for by adjusting the optical signal detection device obtaining the images. In certain embodiments, an adjustment of the optical signal detection device is made after each of a plurality of images are obtained. In certain embodiments, an adjustment, if required by the misalignment correction determination, is made after every image subsequent to the first image (except the last image), and prior to the next consecutive image. In one embodiment, a cervical tissue scan comprising a sequence of 13 images is performed using on-the-fly misalignment correction determination, validation, and camera adjustment, such that the scan is completed in about 12 seconds. Other embodiments comprise obtaining sequences of any number of images in more or less time than indicated here.

Each of steps 228 and 234 of the embodiment of FIG. 2A represents applying a validation algorithm to determine at least the following: (1) whether the misalignment correction can be made, for example, by adjusting the optical signal detection device, and (2) whether the misalignment correction determined is valid. In an exemplary embodiment, the validation algorithm determines that a misalignment correction cannot be executed during an acetowhitening exam conducted on cervical tissue in time to provide sufficiently aligned subsequent images, if either of conditions (a) or (b) is met, as follows: (a) $d_i$, the displacement between the current image "i" and the immediately preceding image "i–1" is greater than 0.55-mm or (b) Sum($d_i$), the total displacement between the current image and the first image in the sequence, "o", is greater than 2.5-mm. If either of these conditions is met, the exam in progress is aborted, and another exam must be performed. Other embodiments may comprise the use of different validation rules.

In the exemplary embodiment above, validation is performed for each determination of misalignment correction by counting how many of the correlation coefficients $c'_r(m,n)$ shown in Equation (5), corresponding to the 16 validation cells, is less than 0.5. If this number is greater than 1, the exam in progress is aborted. Other embodiments may comprise the use of different validation rules. Gradual changes in image features, such as acetowhitening of tissue or changes in glare, cause discrepancies which are reflected in the correlation coefficients of the validation cells, but which do not represent a spatial shift. Thus, in preferred embodiments, the validation is performed as shown in FIG. 2C, where validation cells of consecutive images are used to calculate the correlation coefficients. In other embodiments, the validation is performed as shown in FIG. 2B, where validation cells of a current image, "i", and an initial image of the sequence, "o", are used to calculate the correlation coefficients of Equation (5).

FIGS. 3A-3F depicts a subset of adjusted, filtered images 302, 306, 310, 314, 318, 322 from a sequence of images of a tissue with an overlay of gridlines showing the validation cells used in validating the determinations of misalignment correction between the images, according to an illustrative embodiment of the invention. By performing validation according to FIG. 2C, using consecutive images to calculate the correlation coefficients of Equation (5), the number of validation cells with correlation coefficient below 0.5 for the misalignment-corrected images of FIGS. 3A-3F is 0, 1, 0, 0, and 1 for images 306, 310, 314, 318, and 322, respectively. Since none of the images have more than one coefficient below 0.5, this sequence is successful and is not aborted. This is a good result in this example, since there is no significant tissue movement occurring between the misalignment-corrected images. There is only a gradually changing glare, seen to move with the validation region 304, 308, 312, 316, 320, 324 of each image. In an embodiment in which validation is performed as in FIG. 2B, the number of validation cells with correlation coefficient below 0.5 for the misalignment-corrected images of FIGS. 3A-3F is 3, 4, 5, 5, and 6 for images 306, 310, 314, 318, and 322, respectively. This is not a good result in this example, since the exam would be erroneously aborted, due only to gradual changes in glare or whitening of tissue, not uncompensated movement of the tissue sample.

In a preferred embodiment, validation cells that are featureless or have low signal-to-noise ratio are eliminated from consideration. These cells can produce meaningless correlation coefficients. Featureless cells in a preferred embodiment are identified and eliminated from consideration by examining the deviation of the sum squared gradient of a given validation cell from the mean of the sum squared gradient of all cells as shown in the following exemplary rule:

Rule: If $ssg_1(m,n) < Mean[ssg(m,n)] - STD[ssg(m,n)]$, then set $c'_1(m,n) = 1.0$.

where $c'_1(m,n)$ is the correlation of the given validation cell "1", $ssg_1(m,n) = \Sigma\Sigma I_1^2[p,q]$, m=1 to 4, n=1 to 4, $I_1[p,q]$ is the matrix of values of the given validation cell "1", p=1 to 32, q=1 to 32, the summations $\Sigma\Sigma$ are performed over pixel markers p and q, Mean[ssg(m,n)] is the mean of the sum squared gradient of all 16 validation cells, and STD[ssg(m,n)] is the standard deviation of the sum squared gradient of the given validation cell "1" from the mean sum squared gradient. By setting $c'_1(m,n) = 1.0$ for the given validation cell, the cell does not count against validation of the misalignment correction determination in the rubrics of either step 228 or step 234 of FIG. 2A, since a correlation coefficient of 1.0 represents a perfect match.

If an image has large intensity differences between the upper and lower borders and/or the left and right borders of the image frame field, LoG filtering may result in "wraparound error." A preferred embodiment employs an image blending technique such as "feathering" to smooth border discontinuities, while requiring only a minimal amount of additional processing time.

Figure 4A:
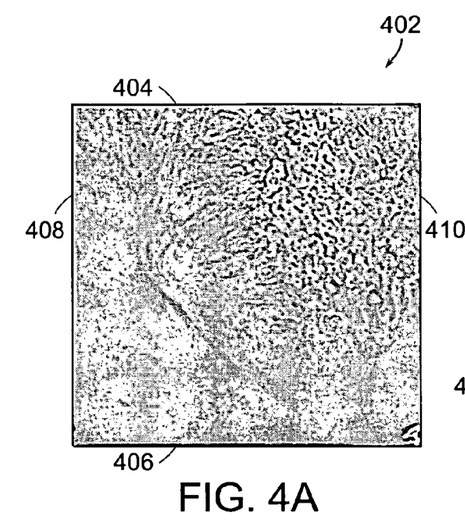
FIG. 4A depicts a sample image after application of a 9-pixel size (9×9) Laplacian of Gaussian filter (LoG 9 filter) on an exemplary image from a sequence of images of tissue according to an illustrative embodiment of the invention.

FIG. 4A depicts a sample image 402 after application of a 9-pixel size [9×9] Laplacian of Gaussian filter (LoG 9 filter) on an exemplary image from a sequence of images of tissue, according to an illustrative embodiment of the invention. The filtered intensity values are erroneous at the top edge 404, the bottom edge 406, the right edge 410, and the left edge 408 of the image 402. Since LoG frequency domain filtering corresponds to cyclic convolution in the space-time domain, intensity discontinuities between the top and bottom edges of an image and between the right and left edges of an image result in erroneous gradient approximations. These erroneous gradient approximations can be seen in the dark stripe on the right edge 410 and bottom edge 406 of the image 402, as well as the light stripe on the top edge 404 and the left edge 408 of the image 402. This often results in a misalignment correction determination that is too small, since changes between the images due to spatial shift are dwarfed by the edge effects. A preferred embodiment uses a "feathering" technique to smooth border discontinuities and reduce "wraparound error."

Feathering comprises removal of border discontinuities prior to application of a filter. In preferred embodiments, feathering is performed on an image before LoG filtering, for example, between steps 206 and 208 in FIG. 2A. In embodiments where LoG filtering is performed in the frequency domain (subsequent to Fourier transformation), feathering is preferably performed prior to both Fourier transformation and LoG filtering. For one-dimensional image intensity functions $I_1(x)$ and $I_2(x)$ that are discontinuous at $x=x_0$, an illustrative feathering algorithm is as follows:

$$I'_1(x) = I_1(x) \cdot f\left(\frac{x - x_0}{d} + 0.5\right) \quad (6)$$

and $$I'_2(x) = I_2(x) \cdot \left(1 - f\left(\frac{x - x_0}{d} + 0.5\right)\right),$$

$$f(x) = \begin{cases} 0 & x < 0 \\ 3x^2 - 2x^3 & 0 \leq x \leq 1 \\ 0 & x > 1, \end{cases}$$

where $I_1'(x)$ and $_2'(x)$ are the intensity functions $I_1(x)$ and $I_2(x)$ after applying the feathering algorithm of Equation (6), and d is the feathering distance chosen. The feathering distance, d, adjusts the tradeoff between removing wraparound error and suppressing image content.

Figure 4B:
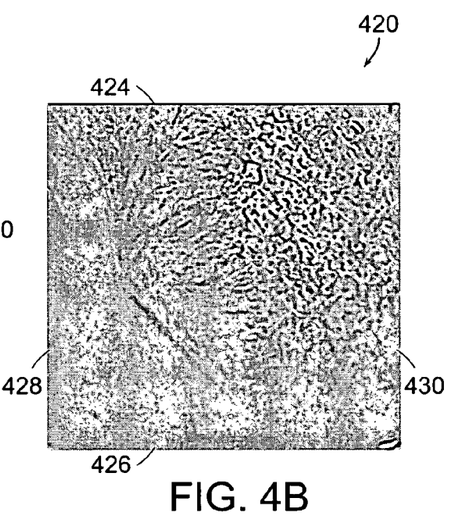
FIG. 4B depicts the application of both a feathering technique and a Laplacian of Gaussian filter on the exemplary unfiltered image used in FIG. 4A to account for border processing effects according to an illustrative embodiment of the invention.

FIG. 4B depicts the application of both a feathering technique and a LoG filter on the same unfiltered image used in FIG. 4A. The feathering is performed to account for border processing effects, according to an illustrative embodiment of the invention. Here, a feathering distance, d, of 20 pixels was used. Other embodiments use other values of d. The filtered image 420 of FIG. 4B does not display uncharacteristically large or small gradient intensity values at the top edge 424, bottom edge 426, right edge 430, or left edge 428, since discontinuities are smoothed prior to LoG filtering. Also, there is minimal contrast suppression of image detail at the borders. Pixels outside the feathering distance, d, are not affected. The use of feathering here results in more accurate determinations of misalignment correction between two images in a sequence of images.

Another method of border smoothing is multiplication of unfiltered image data by a Hamming window. In some embodiments, a Hamming window function is multiplied to image data before Fourier transformation so that the border pixels are gradually modified to remove discontinuities. However, application of the Hamming window suppresses image intensity as well as gradient information near the border of an image.

Figure 5A:
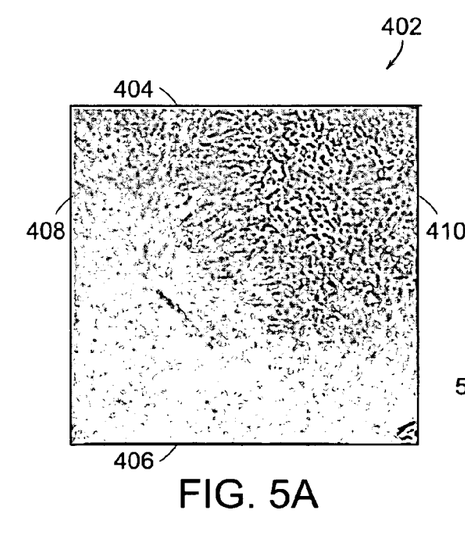
FIG. 5A depicts a sample image after application of a LoG 9 filter on an exemplary image from a sequence of images of tissue according to an illustrative embodiment of the invention.

FIG. 5A is identical to FIG. 4A and depicts the application of a LoG 9 filter on an exemplary image from a sequence of images of tissue according to an illustrative embodiment of the invention. The filtered intensity values are erroneous at the top edge 404, the bottom edge 406, the right edge 410, and the left edge 408 of the image 402.

Figure 5B:
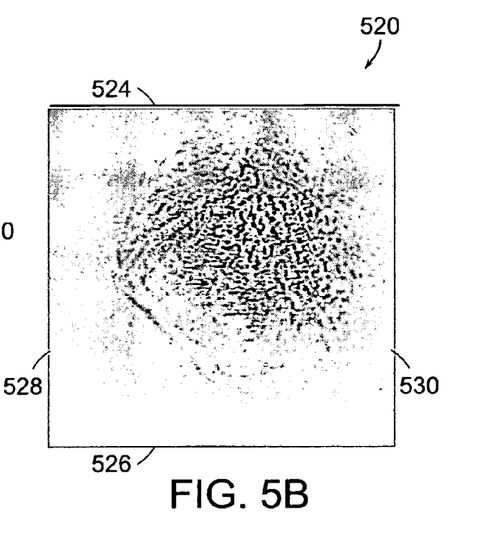
FIG. 5B depicts the application of both a Hamming window technique and a LoG 9 filter on the exemplary unfiltered image used in FIG. 5A to account for border processing effects according to an illustrative embodiment of the invention.

FIG. 5B depicts the application of both a Hamming window and a LoG 9 filter on the same unfiltered image used in FIG. 5A. Hamming windowing is performed to account for border processing effects, according to an illustrative embodiment of the invention. Each of the edges 524, 526, 528, 530 of the image 520 of FIG. 5B no longer show the extreme filtered intensity values seen at the edges 404, 406, 408, 410 of the image 402 of FIG. 5A. However, there is a greater suppression of image detail in FIG. 5B than in FIG. 4B. Thus, for this particular embodiment, application of the feathering technique is preferred over application of Hamming windowing.

A skilled artisan knows other methods of smoothing border discontinuities. Another embodiment comprises removing cyclic convolution artifacts by zero padding the image prior to frequency domain filtering to assure image data at an edge would not affect filtering output at the opposite edge. This technique adds computational complexity and may increase processing time.

Figure 6A:
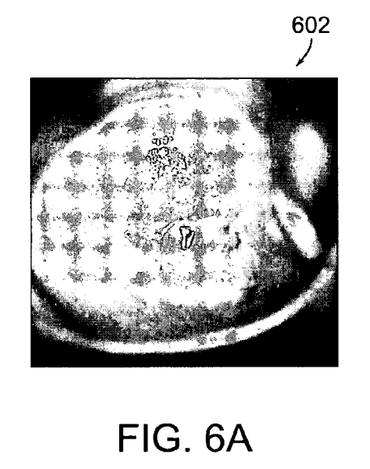
FIGS. 6A-6F depicts the determination of a correction for misalignment between two images using methods including the application of LoG filters of various sizes, as well as the application of a Hamming window technique and a feathering technique according to illustrative embodiments of the invention.
Figure 6B:
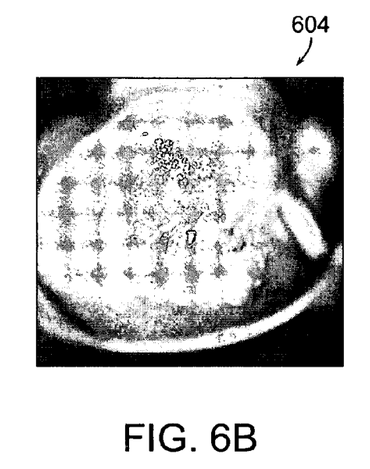
Figure 6C:
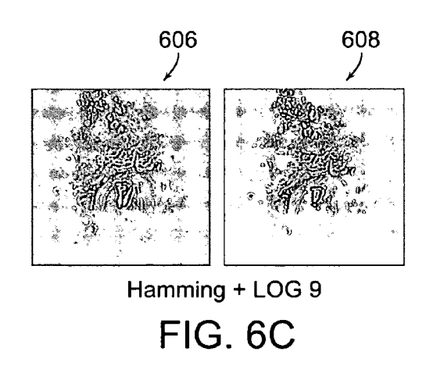
Figure 6D:
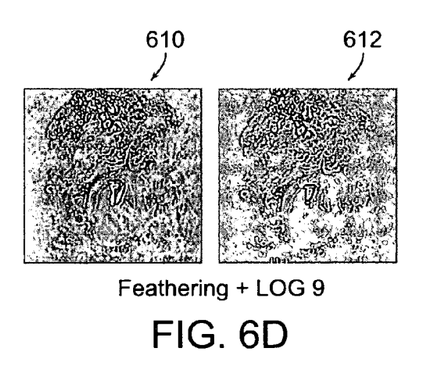
Figure 6E:
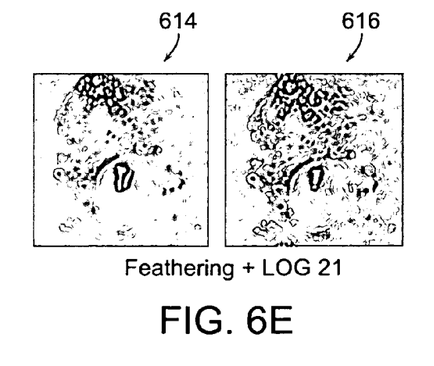
Figure 6F:
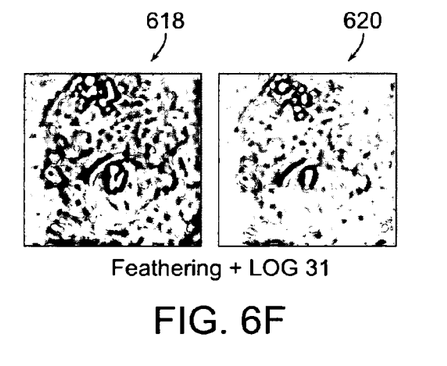

FIGS. 6A-6F depicts the determination of a misalignment correction between two images using methods including the application of LoG filters of various sizes, as well as the application of a Hamming window technique and a feathering technique, according to illustrative embodiments of the invention. Image 602 and image 604 in FIGS. 6A and 6B are consecutive images from a sequence of images of cervix tissue obtained during a diagnostic exam, each with a pixel resolution of about 0.054-mm. FIGS. 6C-6F depicts the application of four different image filtering algorithms: (1) Hamming window with LoG 9 filtering, (2) feathering with LoG 9 filtering, (3) feathering with LoG 21 filtering, and (4) feathering with LoG 31 filtering. Each of these algorithms are implemented as part of a misalignment correction determination and validation technique as illustrated in FIG. 2A and FIG. 2C, and values of $d_x$ and $d_y$ between images 602 and 604 of FIGS. 6A and 6B are determined using each of the four filtering algorithms. For image 602, each of the four different image filtering algorithms (1)-(4) listed above are applied, resulting in images 606, 610, 614, and 618, respectively, each having 256×256 pixels. The four different image filtering algorithms are also applied for image 604, resulting in images 608, 612, 616, and 620, respectively, each having 256×256 pixels. Values of $(d_x, d_y)$ determined using Hamming+LoG 9 filtering are (−7, 0), expressed in pixels. Values of $(d_x, d_y)$ determined using feathering+LoG 9 filtering are (−2,−10). Values of $(d_x, d_y)$ determined using feathering+LoG 21 filtering are (−1,−9). Values of $(d_x, d_y)$ determined using feathering+LoG 31 filtering are (0,−8). All of the displacement values determined using feathering are close in this embodiment, and agree well with visually-verified displacement. However, in this example, the displacement values determined using Hamming windowing are different from those obtained using the other three filtering methods, and result in a misalignment correction that does not agree well with visually-verified displacement. Thus, for this example, feathering works best since it does not suppress as much useful image data.

The effect of the filtering algorithm employed, as well as the choice of validation rules are examined by applying combinations of the various filtering algorithms and validation rules to pairs of sequential images of tissue and determining the number of "true positives" and "false positives" identified. A true positive occurs when a bad misalignment correction determination is properly rejected by a given validation rule. A false positive occurs when a good misalignment correction determination is improperly rejected as a failure by a given validation rule. The classification of a validation result as a "true positive" or a "false positive" is made by visual inspection of the pair of sequential images. In preferred embodiments, whenever true failures occur, the scan should be aborted. Some examples of situations where true failures occur in certain embodiments include image pairs between which there is one or more of the following: a large non-translational deformation such as warping or tilting; a large jump for which motion tracking cannot compute a correct translational displacement; rotation greater than about 3 degrees; situations in which a target laser is left on; video system failure such as blur, dark scan lines, or frame shifting; cases where the image is too dark and noisy, in shadow; cases where a vaginal speculum (or other obstruction) blocks about half the image; other obstructions such as sudden bleeding.

In one embodiment, a set of validation rules is chosen such that true positives are maximized and false positives are minimized. Sensitivity and specificity can be adjusted by adjusting choice of filtering algorithms and/or choice of validation rules.

Table 1 shows the number of true positives (true failures) and false positives (false failures) determined by a validation rule as depicted in FIG. 2A and FIG. 2C where validation is determined using consecutive images. Table 1 shows various combinations of filtering algorithms and validation rules. The four filtering algorithms used are (1) Hamming windowing with LoG 9 filtering, (2) feathering with LoG 9 filtering, (3) feathering with LoG 21 filtering, and (4) feathering with LoG 31 filtering. The values, c'(m,n), correspond to the normalized "auto"-correlation coefficient of Equation (5) whose value must be met or exceeded in order for a validation cell to "pass" in an embodiment. The "Number Threshold" column indicates the maximum number of "failed" validation cells, out of the 16 total cells, that are allowed for a misalignment correction determination to be accepted in an embodiment. If more than this number of validation cells fail, then the misalignment correction determination is rejected.

TABLE 1

True positives and false positives of validation determinations for embodiments using various combinations of filtering algorithms and validation rules.

| | c'(m, n) | Number Threshold | TP | FP |
|---|---|---|---|---|
| Hamming LoG 9 | −0.1 | 1 | 34 | 28 |
| Feathering LoG 9 | −0.1 | 3 | 19 | 17 |
| Feathering LoG 21 | 0.3 | 2 | 46 | 10 |
| | 0.35 | 3 | 52 | 4 |
| Feathering LoG 31 | 0.5 | 3 | 48 | 3 |

For the given set of cervical image pairs on which the methods shown in Table 1 were applied, feathering performs better than Hamming windowing, since there are more true positives and fewer false positives. Among different LoG filter sizes, LoG 21 and LoG 31 performs better than LoG 9 for both tracking and validation here. The LoG 21 filter is more sensitive to rotation and deformation than the LoG 31 filter for these examples. Preferred embodiments for the determination and validation of misalignment corrections between 256×256 pixel portions of images of cervical tissue with pixel resolution of about 0.054-mm employ one or more of the following: (1) use of feathering for image border processing, (2) application of LoG 21 filter, (3) elimination of validation cells with low signal-to-noise ratio, and (4) use of consecutive images for validation.

Equivalents

While the invention has been particularly shown and described with reference to specific preferred embodiments, it should be understood by those skilled in the art that various changes in form and detail may be made therein without departing from the spirit and scope of the invention as defined by the appended claims.

The invention claimed is:

1. A method of validating a correction for an image misalignment, the method comprising the steps of:
   adjusting at least one of two or more images using a correction for an image misalignment between the two or more images;
   defining one or more validation cells, each of which includes a common area of the two or more adjusted images;
   computing for each of the one or more validation cells a measure of displacement between the two or more adjusted images using data from the two or more adjusted images corresponding to each of the one or more validation cells; and
   validating the correction for the image misalignment by comparing at least one of the measures of displacement with a threshold value.

2. The method of claim 1, wherein the images are images of an in-situ tissue sample, and wherein the image misalignment is due at least in part to patient motion.

3. The method of claim 1, wherein the images are images of an in-situ tissue sample that has been treated with a contrast agent.

4. The method of claim 1, wherein the one or more validation cells comprise a subset of a bounded image plane common to the two or more images.

5. The method of claim 4, wherein the one or more validation cells comprise a central portion of the bounded image plane.

6. The method of claim 4, wherein the bounded image plane has an area about four times larger than the total area of the one or more validation cells.

7. The method of claim 1, wherein the two or more images are consecutive images.

8. The method of claim 1, wherein the validating step comprises eliminating from consideration one or more of the measures of displacement for one or more of the one or more validation cells.

9. The method of claim 8, wherein the eliminating of the one or more measures of displacement comprises calculating a sum squared gradient for at least one of the one or more validation cells.

10. A method of validating a correction for an image misalignment, the method comprising the steps of:
    defining one or more validation cells within a bounded image plane;
    computing for each of the one or more validation cells a measure of displacement between two or more images bound by the image plane using data from the two or more images corresponding to each of the one or more validation cells;
    validating a correction for an image misalignment between the two or more images by comparing at least one of the measures of displacement with the correction.

11. A method of validating a correction for an image misalignment, the method comprising the steps of:
    obtaining a plurality of sequential images of a sample using an optical signal detection device;
    determining a correction for a misalignment between at least two of the sequential images, the misalignment due at least in part to a movement of the sample; and
    validating the correction between at least a first image and a second image of the plurality of sequential images;
    wherein the determination of a correction for a misalignment between a first and a second image and the validation of said correction are performed in less than about one second.

12. The method of claim 11, wherein the sample is an in-situ tissue sample and wherein the misalignment is due at least in part to patient motion.

13. The method of claim 11, further comprising the step of applying a contrast agent to the sample.

14. The method of claim 11, further comprising the step of:
    adjusting the optical signal detection device using the correction.

* * * * *